US008883173B2

(12) United States Patent
Reyrat et al.

(10) Patent No.: US 8,883,173 B2
(45) Date of Patent: Nov. 11, 2014

(54) **SYNTHETIC ANTIGENIC PEPTIDES AND LIPOPEPTIDES DERIVED FROM *MYCOBACTERIUM AVIUM* SUBSP. *PARATUBERCULOSIS***

(75) Inventors: Jean-Marc Reyrat, Vanves (FR); Sylvie Bay, Paris (FR); Franck Biet, Notre Dame d'Oe (FR)

(73) Assignees: Institut National de la Sante et de la Recherche Medicale (Inserm), Paris (FR); Institut National de la Recherche Agronomique, Paris (FR); Institut Pasteur, Paris (FR); Jean-Marc Reyrat, Vanves (FR)

( * ) Notice: Subject to any disclaimer, the term of this patent is extended or adjusted under 35 U.S.C. 154(b) by 932 days.

(21) Appl. No.: 12/739,607

(22) PCT Filed: Oct. 24, 2008
(Under 37 CFR 1.47)

(86) PCT No.: PCT/IB2008/003396
§ 371 (c)(1),
(2), (4) Date: Jul. 19, 2011

(87) PCT Pub. No.: WO2009/053844
PCT Pub. Date: Apr. 30, 2009

(65) Prior Publication Data

US 2011/0311563 A1 Dec. 22, 2011

(30) Foreign Application Priority Data

Oct. 26, 2007 (EP) .................................... 07291296

(51) Int. Cl.

| | |
|---|---|
| ***A61K 39/04*** | (2006.01) |
| ***C12Q 1/00*** | (2006.01) |
| ***A61K 39/00*** | (2006.01) |
| ***C07K 14/35*** | (2006.01) |
| ***A61K 38/08*** | (2006.01) |
| ***A61K 38/16*** | (2006.01) |
| ***G01N 33/569*** | (2006.01) |
| ***C07K 7/06*** | (2006.01) |

(52) U.S. Cl.
CPC ............ *G01N 33/5695* (2013.01); *C07K 14/35* (2013.01); *A61K 38/08* (2013.01); *A61K 38/164* (2013.01); *C07K 7/06* (2013.01)
USPC ....... 424/248.1; 424/9.1; 424/9.2; 424/184.1; 424/185.1; 424/234.1; 424/130.1; 424/139.1; 424/164.1; 435/4; 435/7.1

(58) Field of Classification Search
USPC .................. 424/9.1, 9.2, 184.1, 185.1, 234.1, 424/248.1, 130.1, 139.1, 164.1; 435/4, 7.1
See application file for complete search history.

(56) References Cited

PUBLICATIONS

Thibault, et al., "New Variable-Number Tandem-Repeat Markers for Typing *Mycobacterium avium*. . . ", Journal of Clinical Microbiology, 45, pp. 2404-2410, 2007.
Biet, et al., "Lipopentapeptide Induces a Strong Host Humoral Response . . . ", Vaccine, 26, pp. 257-268, 2007.
Eckstein, et al., "A Major Cell Wall Lipopeptide of *Mycobacterium avium* Subspecies *Paratuberculosis*", Journal of Biological Chemistry, 281, pp. 5209-5215, 2006.
Cangelosi, et al., "Biology of Waterborne Pathogenic Mycobacteria", World Health Organization—U.S. Environmental Protection Agency, Chapter 4, pp. 39-54, 2004.
Eckstein, et al., "Lipidomics of *Mycobacterium avium*. . . ", Abstracts of the General Meeting of the American Society for Microbiology, 105, p. 577, 2005.
Moody, et al., "T Cell Activation by Lipopeptide Antigens", American Association for the Advancement of Science, 303, pp. 527-531, 2004.

*Primary Examiner* — Rod P Swartz
(74) *Attorney, Agent, or Firm* — Morgan, Lewis & Bockius LLP

(57) ABSTRACT

The current invention relates to the diagnosis and treatment of diseases resulting from infections by *Mycobacterium avium* subsp. *paratuberculosis*. In particular the invention relates to the use of an antigen selected among (a) a synthetic peptide 5P having the following formula: DPhe-NMeVal-Ile-Phe-Ala-OMe (SEQ ID NO: 1); (b) a lipopeptide L5P consisting of the synthetic peptide a) wherein the N-terminal phenylalanine residue is N-acylated with an eicosanoic acid acyl chain; (c) a variant of peptide a) or lipopeptide b) able to react with anti-*Mycobacterium paratuberculosis* antibodies; for in vitro detection or quantification of specific anti-*Mycobacterium paratuberculosis* antibodies in a biological sample.

12 Claims, 7 Drawing Sheets

Map K-10

A

B

A

B

C

A

B

Figure 1:
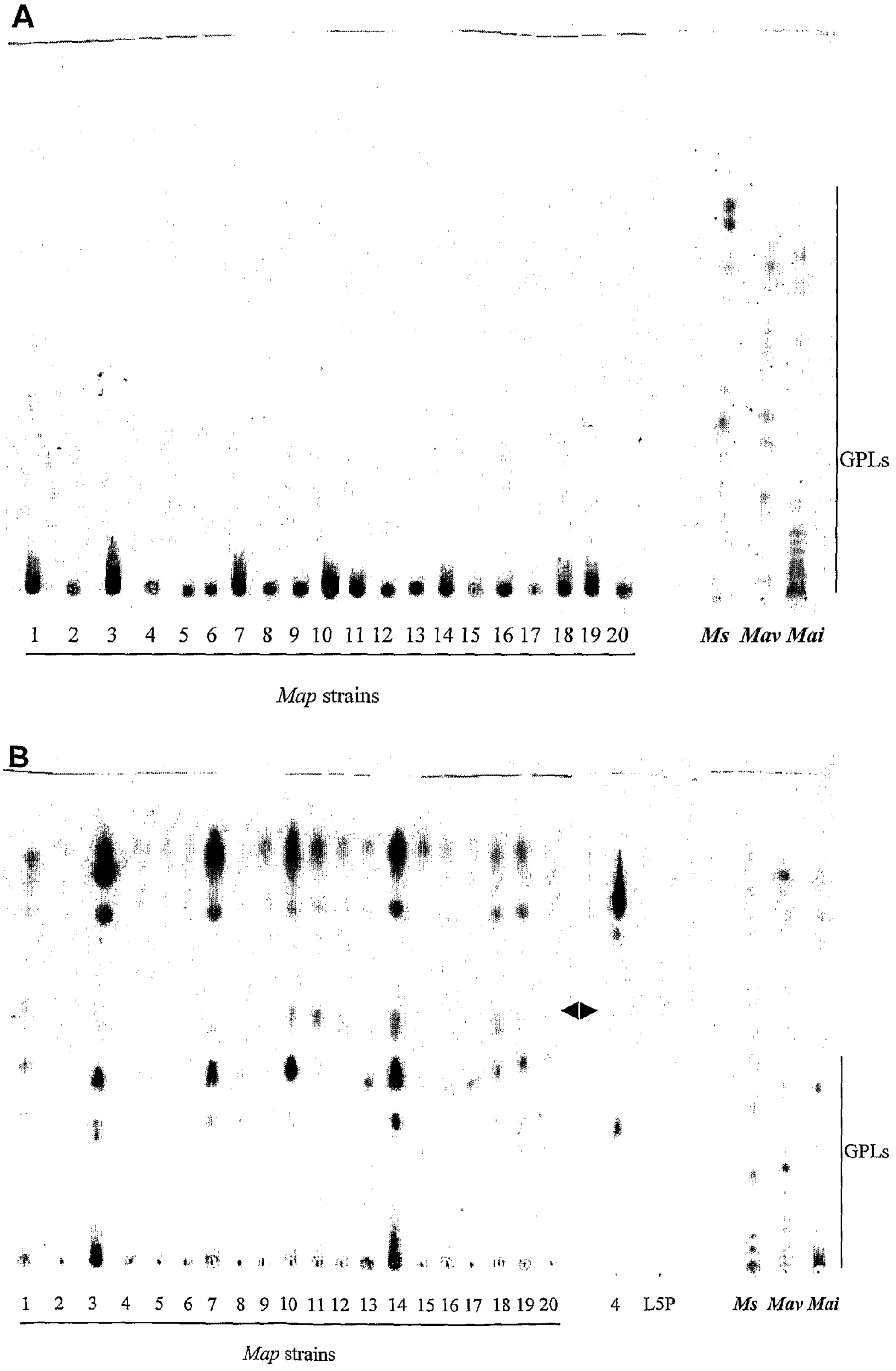

SEQUENCE LISTING

<160> NUMBER OF SEQ ID NOS: 20

<210> SEQ ID NO 1
<211> LENGTH: 5
<212> TYPE: PRT
<213> ORGANISM: artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 1

Phe Val Ile Phe Ala
1               5

<210> SEQ ID NO 2
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 2

Phe Val Ile Phe Ala
1               5

<210> SEQ ID NO 3
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylanine
<220> FEATURE:
<221> NAME/KEY: MISC_FEATURE
<222> LOCATION: (5)..(5)

<223> OTHER INFORMATION: O-methylation

<400> SEQUENCE: 3

Phe Val Ile Phe Ala
1 5

<210> SEQ ID NO 4
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: O-methylation

<400> SEQUENCE: 4

Phe Val Ile Phe Ala
1 5

<210> SEQ ID NO 5
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation

<400> SEQUENCE: 5

Phe Val Ile Phe Ala
1 5

<210> SEQ ID NO 6
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine

<400> SEQUENCE: 6

Phe Val Ile Phe Ala
1 5

<210> SEQ ID NO 7
<211> LENGTH: 5
<212> TYPE: PRT
<213> ORGANISM: Artificial
<220> FEATURE:
<223> OTHER INFORMATION: Synthetic peptide

<400> SEQUENCE: 7

Phe Val Ile Phe Ala
1 5

<210> SEQ ID NO 8
<211> LENGTH: 5
<212> TYPE: PRT

<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: N-methylation

<400> SEQUENCE: 8

Phe Val Ile Phe Ala
1               5

<210> SEQ ID NO 9
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-acetylation
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 9

Phe Val Ile Phe Ala
1               5

<210> SEQ ID NO 10
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (1)..(1)
<223> OTHER INFORMATION: N-acetylation
<220> FEATURE:
<221> NAME/KEY: MISC_FEATURE
<222> LOCATION: (5)..(5)
<223> OTHER INFORMATION: O-methylation

<400> SEQUENCE: 10

Phe Val Ile Phe Ala
1               5

<210> SEQ ID NO 11
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-acetylation
<220> FEATURE:

```
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 11

Phe Val Ile Phe Ala
1               5


<210> SEQ ID NO 12
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (1)..(1)
<223> OTHER INFORMATION: N-acetylation
<220> FEATURE:
<221> NAME/KEY: MISC_FEATURE
<222> LOCATION: (2)..(2)
<223> OTHER INFORMATION: N-methylation

<400> SEQUENCE: 12

Phe Val Ile Phe Ala
1               5


<210> SEQ ID NO 13
<211> LENGTH: 21
<212> TYPE: DNA
<213> ORGANISM: Artificial
<220> FEATURE:
<223> OTHER INFORMATION: Primer 1

<400> SEQUENCE: 13

cgaggacttc ggcgagccgg t                                                21


<210> SEQ ID NO 14
<211> LENGTH: 23
<212> TYPE: DNA
<213> ORGANISM: Artificial
<220> FEATURE:
<223> OTHER INFORMATION: Primer 2

<400> SEQUENCE: 14

tcatgtaggc gatgtcgtcg ggc                                              23


<210> SEQ ID NO 15
<211> LENGTH: 28
<212> TYPE: DNA
<213> ORGANISM: Artificial
<220> FEATURE:
<223> OTHER INFORMATION: Primer 3

<400> SEQUENCE: 15

attgagcgca gccagcatcc ccaagccc                                         28


<210> SEQ ID NO 16
<211> LENGTH: 26
<212> TYPE: DNA
<213> ORGANISM: Artificial
```

<220> FEATURE:
<223> OTHER INFORMATION: Primer 4

<400> SEQUENCE: 16
ttgaccagga cgaaaaatcg gccgcc 26

<210> SEQ ID NO 17
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-acylation with eicosanoic acid
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 17

Phe Val Ile Phe Val
1               5

<210> SEQ ID NO 18
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acylation with eicosanoic acid
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 18

Phe Val Ile Phe Val
1               5

<210> SEQ ID NO 19
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acylation with eicosanoic acid
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (5)..(5)

-continued

```
<223> OTHER INFORMATION: O-methylation

<400> SEQUENCE: 19

Phe Val Ile Phe Val
1               5


<210> SEQ ID NO 20
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acylation with eicosanoic acid
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation

<400> SEQUENCE: 20

Phe Val Ile Phe Val
1               5
```

SYNTHETIC ANTIGENIC PEPTIDES AND LIPOPEPTIDES DERIVED FROM *MYCOBACTERIUM AVIUM* SUBSP. *PARATUBERCULOSIS*

RELATED APPLICATIONS

The present application is a U.S. National Phase Application of International Application No. PCT/IB2008/003396 (filed Oct. 24, 2008), which claims priority to European Patent Application No. 07291296.7 (filed Oct. 26, 2007), all of which are hereby incorporated by reference in their entirety.

SEQUENCE LISTING

A computer readable text file, entitled "045636-5133-SequenceListing.txt," created on or about Apr. 22, 2010 with a file size of about 10 kb contains the sequence listing for this application and is hereby incorporated by reference in its entirety.

The current invention relates to the diagnosis and treatment of diseases resulting from infections by *Mycobacterium avium* subsp. *paratuberculosis*.

Mycobacteria are well known for their acid-fastness and peculiar lipid-rich cell wall. The most studied pathogenic species include (i) *M. tuberculosis*, (ii) *M. ulcerans* and (iii) *M. leprae* (WHO (WORLD HEALTH ORGANIZATION), WHO report 2006 Geneva, WHO/HTM/TB/2006.2362, 2006; LOCKWOOD and SUNEETHA, Bull World Health Organ, 83, 230-235, 2005), the disease causing agents of (i) tuberculosis, (ii) indolent nonulcerated nodules, plaques and ulcerated lesions and (iii) leprosy respectively.

*M. avium* subsp. *avium* (May) and *M. avium* subsp. *paratuberculosis* (Map) are two closely related species belonging to the *M. avium-intracellulare* complex (MAC) that also includes *M. avium* subsp. *intracellulare* (Mai), *M. avium* subsp. *hominissuis* (Mah) and *M. avium* subsp. *sylvaticus* (Mas).

Infections by Mav are among the most frequent opportunistic infections found in patients with chronic respiratory infections and in patients suffering from acquired immunodeficiency syndrome (INDERLIED et al., Clin Microbiol Rev, 6, 266-310, 1993; HORSBURGH, N Engl J Med, 324, 1332-1338, 1991).

Map is the causative agent of paratuberculosis or Johne's disease in ruminants and similar diseases in other animals. This bacterium is responsible for significant economic losses in the agricultural sector world-wide due to the characteristic wasting disease associated with infection by this bacterium. Map is a slow-growing mycobacteria and requires fastidious culture conditions to grow. In general it takes more than 2 months to obtain a colony on a Petri-dish from which biochemical or genetic studies can be made and also requires mycobactin supplementation for its growth (THOREL et al., Int J Syst Bacteriol, 40, 254-260, 1990).

In addition to domesticated farm animals Map also infects wild animals such as red deer, rabbits, bisons and buffalo (BIET et al., Vet Res, 36, 411-436, 2005).

Map targets the digestive system, which lead to weight loss and death (CLARKE, J Comp Pathol, 116, 217-261, 1997). The virulence mechanisms of Map are not yet fully characterized but it is hoped that by the sequencing of its genome and the creation of genetic tools will open the way for such studies.

Although at the present time still unconfirmed, several reports have also suggested Map is associated with Crohn's disease in humans (CHACON et al., Annu Rev Microbiol, 58, 329-363, 2004).

Despite the fact that Map and Mav induce entirely different disease phenotypes, the comparison of their complete genome sequences has confirmed that they are highly homologous and closely related (BANNANTINE et al., J Clin Microbiol, 40, 1303-1310, 2002).

This close relationship raises problems for specific immunodetection of Map. Thus far, the detection of serum antibodies against Map is achieved using different crude fractions of the bacterium as antigen (COLLINS et al., Clin Diagn Lab Immunol, 12, 685-692, 2005). However, false-positive reactions can occur as a result of the presence of related bacteria in the environment. To diminish cross-reacting antibodies and to increase the specificity of the ELISA, the serum is generally pre-absorbed with crude fractions from another mycobacterium, *M. phlei* (YOKOMIZO et al., J Vet Med Sci, 53, 577-584, 1991). This supplementary step is, however, expensive, time consuming and another barrier to the establishment of a reproducible diagnostic test.

Diagnostic tests aimed at the detection of an early (T-cell-mediated) immune response, e.g. a skin test and a gamma-interferon assay, suffer from the same drawback. The antigens routinely used for these tests, avian or Johnin PPD, produce non-specific reactions in young animals (STABEL et al., J Vet Diagn Invest, 8, 469-473, 1996).

Glycopeptidolipids (GPLs) represent major antigens of Mav. GPLs can represent more than 70% of the lipids exposed at the bacterial surface and are highly antigenic (BILLMAN-JACOBE, Current Science, 86, 11-114, 2004). They have a glycosylated lipopeptide core that is variably modified by methylation and acetylation. More precisely, the GPL structure is based on a tripeptide-aminoalcohol (D-Phe-D-allo-Thr-D-Ala-L-alaninol) linked to a fatty acyl residue. This lipopeptide core is substituted with a 6-deoxytalosyl (dTal) unit linked to the allo-Thr residue and with an O-methylated rhamnosyl unit linked to the terminal alaninol residue. The dTal residue can be acetylated on position 3 or 4, whereas the fatty acyl moiety and the rhamnosyl residue can be modified with one and two methyl groups on position 3 or 4, respectively. In some cases, GPLs can be further glycosylated by the addition of an extra saccharidic appendage on the existing talose. GPLs have been shown to induce the release of prostaglandin E2 and to interfere with the interaction of mycobacteria with human monocytes/macrophages (BARROW et al., Infect Immun, 63, 126-133, 1995; VILLENEUVE et al., J Biol Chem, 278, 51291-51300, 2003). GPLs also influence bacterial aggregation (DESHAYES et al., J Bacteriol, 187, 7283-7291, 2005; ETIENNE et al., Microbiology, 148, 3089-3100, 2002) and are required for sliding motility, biofilm formation and for maintaining cell wall integrity (ETIENNE et al., Microbiology, 148, 3089-3100, 2002; RECHT and KOLTER, J Bacteriol, 183, 5718-5724, 2001). The mechanism of GPL synthesis involves approximately fifteen genes. In *M. smegmatis*, these genes are contiguous and delineate a GPL locus (RIPOLL et al., BMC Genomics, 8, 114, 2007). The majority of these genes have been experimentally characterized while the function of a number of other genes has been inferred in silico to date.

GPLs have been used to diagnose Mav infections, and differences in their structure have been exploited to classify related Mav strains.

Although Mav and Map are phylogenetically closely related, there have been conflicting reports concerning the production of GPLs by strains of the Map subspecies (LANEELLE and ASSELINEAU, Biochim Biophys Acta, 59, 731-732, 1962; OHENE-GYAN et al., Comp Immunol Microbiol Infect Dis, 18, 161-170, 1995; CAMPHAUSEN et al., Proc Natl Acad Sci USA, 82, 3068-3072, 1985; LANEELLE et al., Bull Soc Chim Biol (Paris), 2133-2134, 1965).

It has been recently reported by ECKSTEIN et al. (ECKSTEIN et al., J Biol Chem, 281, 5209-5215, 2006) that the Map K-10 strain, which lacks GPLs and is missing some of the genes responsible for their biosynthesis, produces a cell-wall associated lipid component, termed Para-LP-01, which is absent from the Mav strain 2151. These authors further characterized Para-LP-01 as a lipopeptide complex or family, comprising a mixture of lipopeptides having a same pentapeptide core (D-Phe-N-Me-L-Val-L-Ile-L-Phe-L-Ala) linked to a series of saturated fatty acids, ranging from C16 to C22, and dominated by C20. They also tested the reactivity of a Para-LP-01 preparation, against bovine sera from animals infected or not with *Mycobacterium paratuberculosis*. Among 6 sera from infected animals, 5 reacted positively, although at different levels, with Para-LP-01; on the other hand one among 3 sera from uninfected animals reacted faintly with Para-LP-01. The reactivity of sera from animals infected with mycobacteria other than *Mycobacterium paratuberculosis* was not tested.

The inventors have sought to establish whether the production of lipopeptides, and more specifically of Para-LP-01 was a particularity of the K-10 strain, or was more widespread in Map. To do this, they analyzed a large panel (see Table 1) of well-characterized Map isolates obtained from different hosts and from different geographic origins (THIBAULT et al., J Clin Microbiol, 45, 2404-2410, 2007) for Para-LP-01 production.

They found that all these Map isolates were able to produce lipid compounds, which they identified using thin layer chromatography and MALDI-TOF mass spectrometry, as similar to Para-LP-01. In contrast, they did not find these compounds in lipid extracts from strains of the species *Mycobacterium smegmatis* and *Mycobacterium avium*, used as controls.

Therefore it appears that the production of these lipopeptides is a distinguishing trait between Map and Mav, which could be used to determine whether an animal has been infected with Map.

However, these lipopeptides obtained from cultures of Map organisms were at most 85% pure. Thus it could not be excluded that the immunoreactivity of these compounds was due to unidentified contaminants.

The inventors have thus synthesized the D-Phe-N-Me-L-Val-L-Ile-L-Phe-L-Ala pentapeptide, N-terminally linked to a C20 saturated fatty acid (eicosanoic acid).

This synthetic pentapeptide will be designated hereinafter as L5P.

They found that the immunoreactivity of L5P is similar to the one of the native Para-LP-01 preparation. Further, they found that, surprisingly, the $C_{20}$ saturated fatty acid was not necessary for the immunoreactivity of the L5P, and that the pentapeptide alone (hereinafter designated as 5P) was recognized at least as efficiently, and in some cases was better recognized than the whole L5P.

These findings of the inventors allow them to propose the use of 5P or L5P, as well as variants and derivatives thereof for the diagnosis or treatment of Map-associated diseases.

According to a first aspect, the invention relates to the use of an antigen selected among:

a) a synthetic peptide 5P having the following formula:

DPhe-NMeVal-Ile-Phe-Ala-OMe (SEQ ID NO: 1);

b) a lipopeptide L5P consisting of the synthetic peptide a) wherein the N-terminal phenylalanine residue is N-acylated with an eicosanoic acid acyl chain;

c) a variant of peptide a) or lipopeptide b) able to react with anti-Map antibodies;

for the in vitro detection or quantification of specific anti-Map antibodies in a biological sample.

"Specific anti-Map antibodies" herein refers to antibodies which are directed against antigenic determinants present in *Mycobacterium paratuberculosis* and absent in other species of mycobacteria, i.e. said antibodies react with *Mycobacterium paratuberculosis* and do not cross-react with other mycobacteria. Preferably, said antibodies belong to the IgM, IgG1 or IgG2 class.

According to a particular embodiment, there is provided a method for detecting or quantifying specific anti-Map antibodies in a biological sample, wherein said method comprises contacting said biological sample with a compound selected among:

a) a synthetic peptide 5P having the following formula:

DPhe-NMeVal-Ile-Phe-Ala-OMe (SEQ ID NO: 1)

b) a lipopeptide L5P consisting of the synthetic peptide a) wherein the N-terminal phenylalanine residue is N-acylated with an eicosanoic acid acyl chain;

c) a variant of peptide 5P or lipopeptide L5P able to react with said anti-Map antibodies;

under conditions allowing the formation of an antigen-antibody complex, and detecting or quantifying said antigen-antibody complex.

Examples of variants of peptide 5P or lipopeptide L5P include the following peptides:

Phe-NMeVal-Ile-Phe-Ala-OMe; (SEQ ID NO: 2)

DPhe-Val-Ile-Phe-Ala-OMe; (SEQ ID NO: 3)

Phe-Val-Ile-Phe-Ala-OMe; (SEQ ID NO: 4)

DPhe-NMeVal-Ile-Phe-Ala; (SEQ ID NO: 5)

DPhe-Val-Ile-Phe-Ala; (SEQ ID NO: 6)

Phe-Val-Ile-Phe-Ala; (SEQ ID NO: 7)

Phe-NMeVal-Ile-Phe-Ala (SEQ ID NO: 8)

Other examples of variants of peptide 5P or lipopeptide L5P include the variants obtainable from the peptides SEQ ID NO: 1 to SEQ ID NO: 8 by one or more of the following modifications:

a) N-acylation of the N-terminal phenylalanine residue with a C1 to C30 acyl group, preferably an aliphatic acyl group; non limitative examples of preferred N-acylated variants include:

N-acetylated variants, such as;

AcNH-DPhe-NMeVal-Ile-Phe-Ala-OMe (SEQ ID NO: 9) also designated hereinafter as designated hereinafter as Ac5P;

AcNH-DPhe-Val-Ile-Phe-Ala-OMe (SEQ ID NO: 10)

AcNH-Phe-NMeVal-Ile-Phe-Ala-OMe; (SEQ ID NO: 11)

AcNH-DPhe-NMeVal-Ile-Phe-Ala (SEQ ID NO: 12)

lipopeptides derived from the peptides SEQ ID NO: 1 to SEQ ID NO: 8 by N-acylation with a saturated or unsaturated fatty acid acyl chain, (i.e a C4 to C28 acyl chain), preferably a C18 to C22 fatty acid acyl chain, still more preferably an eicosanoic acid acyl chain;

b) replacement of the methyl ester of the C-terminal alanine residue by another alkyl ester, in particular an ethyl ester or butyl ester, or amidation of the C-terminal alanine residue;

c) replacement of one or more of the L-aminoacids of the peptidic chain by a D-amino acid;

d) modification of the peptidic linkages in order to ensure a better stability of the peptide, etc.

In the formulae indicated herein, the amino-acids are designated by their usual symbols in the three-letters code; DPhe designates D-phenylalanine, NMeVal designates N-methylated valine, Ala-OMe designates O-methylated alanine, AcNH-DPhe designates N-acetylated D-phenylalanine.

The peptide 5P as well as the variants of peptide 5P or lipopeptide L5P indicated above are also encompassed by the present invention. These compounds can be prepared by conventional processes for synthesizing proteins, such as, for example, solid phase peptide synthesis.

If wished, they can be labelled or coupled to a solid support. Labels and solid supports suitable for immunoassays, and methods for labelling peptides as well as for coupling them to said supports are known in themselves. One of skill in the art will choose the most appropriate label or support depending on the technique that he intends to use to detect the antigen/antibody complex.

The antigen/antibody complex formed can be detected or quantified by a variety of methods using standard techniques, including, by way of non-limitative examples, enzyme-linked immunosorbent assay (ELISA) or other solid phase immunoassays, radioimmunoassay, electrophoresis, immunofluorescence, or Western blot.

The biological sample is preferably a serum or plasma sample. It may also be a fecal sample or a milk sample.

The peptide 5P, the lipopeptide L5P, or variants thereof, as defined above, can also be used for evaluating in vitro or in vivo the T-cell immune response directed against Map. This can be done by the usual techniques for in vitro or in vivo detection of the cellular immune response.

For instance, an in vitro method using the peptide 5P, the lipopeptide L5P, or a variant thereof for evaluating the T-cell immune response of an individual with respect to Map, comprises incubating peripheral blood mononuclear cells (PBMCs) of said individual with said peptide 5P, said lipopeptide L5P, or said variant, under conditions allowing the activation of the T lymphocytes present in said PBMCs, and detecting the activated T lymphocytes.

The detection of the activated T lymphocytes can be carried out by conventional methods, generally by determination of the cytokines, in particular gamma-interferon, produced by the lymphocytes upon activation. According to a preferred embodiment, said detection is carried out by an ELISPOT assay.

For in vivo detection, the peptide 5P, the lipopeptide L5P, or variants thereof can be used for preparing a composition for detecting delayed-type hypersensitivity cell-mediated immune responses by skin tests.

The methods of the present invention are in particular useful for diagnosing whether a mammal has been infected with Map, and to establish differential diagnosis between infection with Map and infection with other mycobacteria such as Mai, Mav and *M. bovis*.

They are applicable to any mammalian species prone to infection with Map, including in particular farm animals, such as cows, sheep and goats, as well as wild animals such as red deer, rabbits, bisons, buffalo, and including also humans.

The chemically synthesized 5P, L5P and derivatives of the invention have many advantages over the extracted/purified preparations which were proposed in the prior art for detection of Map. In particular, they allow to avoid false-positive reactions occurring due to contamination by compounds shared by other mycobacterium species. Preparation of synthetic peptides and lipopeptides is less expensive and may be standardized contrary to the preparation of crude extracts that required complicated culture of various Map strains. Further, 5P and L5P are far more specific than the crude cell wall extract of Map currently employed as a paratuberculosis diagnostic test, while being as sensitive, although they involve a single antigen.

The present invention also provides kits for performing the above described-methods of detection of humoral or cellular immunity against Map. These kits typically comprise, besides the 5P, L5P or derivative thereof, other reagents allowing to conduct the immunoassay.

The peptide 5P, the lipopeptide L5P, or variants thereof can also be used for preparing immunogenic compositions, for instance vaccines directed against Map.

For this purpose, they may be associated with carriers and/or immunoadjuvants. Such carriers and immunoadjuvants are well known to those of ordinary skill in the art. Carriers are typically large macromolecules such as proteins, polysaccharides, amino acid copolymers, liposomes. Although these carriers have often in themselves an immunoadjuvant function, additional adjuvants may be used, such as, for instance aluminium salts, muramylpeptides, or CpG oligodeoxynucleotides. The choice of the most appropriate carrier or adjuvant depends in particular on the type of immune response that one wishes to induce. For instance, for inducing preferably a humoral immune response, one will choose alum, saponins or bacterial Toxins. For inducing a cellular immune response, one will choose oligonucleotides comprising CpG motifs, or nucleoside analogues such as imidazoquinolines.

If wished, they can also be associated with any other vaccine antigen.

The present invention also provides antibodies directed against the peptide 5P, the lipopeptide L5P, or variants thereof. Said antibodies may be obtained by immunizing an animal against the peptide 5P, the lipopeptide L5P, or their variants. They may also be purified by affinity from the sera of animals infected with Map, for instance by affinity chromatography using the peptide 5P, the lipopeptide L5P, or their variants.

The inventors have further identified genetic regions of Map involved in the biosynthesis of the Map specific lipopeptide, and have designed primers allowing to differentiate Map from related mycobacteria. This set of primers allows the amplification of the mps1-mps2 junction in the genome of mycobacteria other than Map while it does not give any amplification product in Map strains.

A further object of the present invention is a set of primers defined by the following sequences:

```
5' CGA GGA CTT CGG CGA GCC GGT      (SEQ ID NO: 13)

5' TCA TGT AGG CGA TGT CGT CGG GC   (SEQ ID NO: 14)
```

The invention also provides a method for determining whether a mycobacterium belongs to the Map family, wherein said method comprises performing PCR amplification on a biological sample containing nucleic acid from said mycobacterium, using a set of primers allowing the detection of the mps1-mps2 junction in the mycobacterial genome.

Preferably, said set of primers consist of a primer having the sequence 5' CGA GGA CTT CGG CGA GCC GGT (SEQ ID NO: 13) and a primer having the sequence 5' TCA TGT AGG CGA TGT CGT CGG GC (SEQ ID NO: 14).

The present invention also provides a method for detecting the presence of *Mycobacterium avium* subsp. *paratuberculosis* in a sample, comprising the steps of:

a) amplification of a reaction mixture comprising DNA isolated from said sample and at least one set of primers for detection of the gap-mbtH junction;

b) amplification of a reaction mixture comprising DNA isolated from said sample and at least one set of primers for detection of the mps1-mps2 junction;

c) determining the presence of *Mycobacterium avium* subsp. *paratuberculosis* in a sample if a product of a predetermined size is produced in step a) but absent from step b).

The present invention will be further illustrated by the additional description which follows, which refers to examples describing the synthesis of antigens of the invention, and their specific reactivity with anti-Map antibodies. It should be understood however that these examples are given only by way of illustration of the invention and do not constitute in any way a limitation thereof.

FIGURES

FIG. 1. Thin-layer chromatography analysis of the crude lipid extracts of *M. smegmatis* (Ms), *M. avium* subsp. *avium* 104 (Mav), *M. avium* subsp. *intracellulare* ATCC 13950 (Mai) and *M. avium* subsp. *paratuberculosis* (Map). The Map strain numbers refer to the numbers strain detailed in Table 1. (A) TLC were run in chloroform/methanol (90:10) and developed by spraying the plates with 0.2% anthrone (B) TLC were run in chloroform/methanol (96:4) and the lipids identified and developed by spraying the plates with or 10% copper sulfate. The locations of GPLs and of L5P (arrowheads) are indicated. Map strains N° 20 to 39 were producing similar patterns to the Map strains presented in this figure (data not shown).

Figure 2:
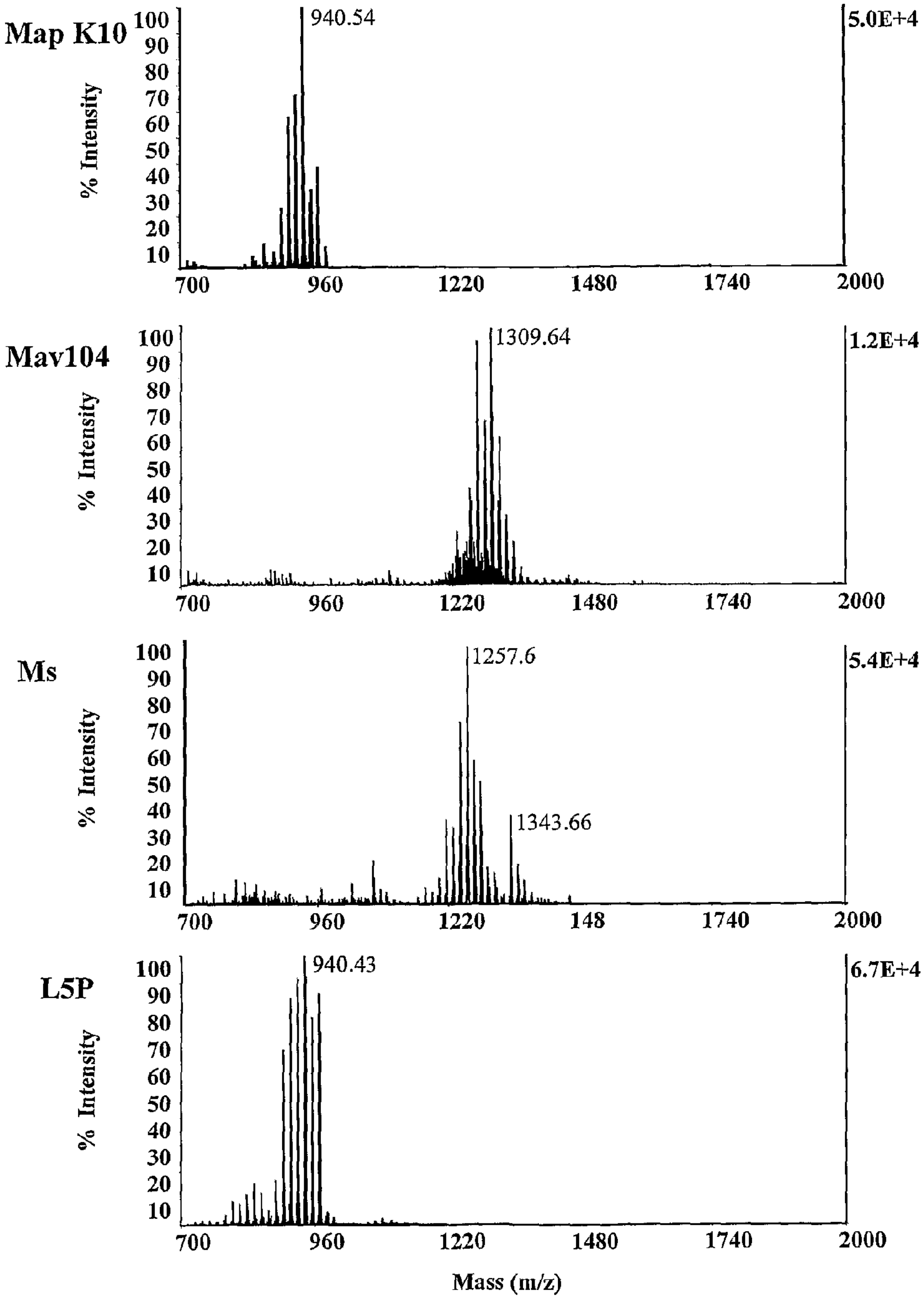

FIG. 2. MALDI-TOF mass spectrometry analyses of the native lipids of *M. smegmatis* (Ms), *M. avium* subsp. *avium* (Mav104) and *M. avium* subsp. *paratuberculosis* (Map) and of the lipopeptide (L5P) chemically synthesized.

Figure 3:
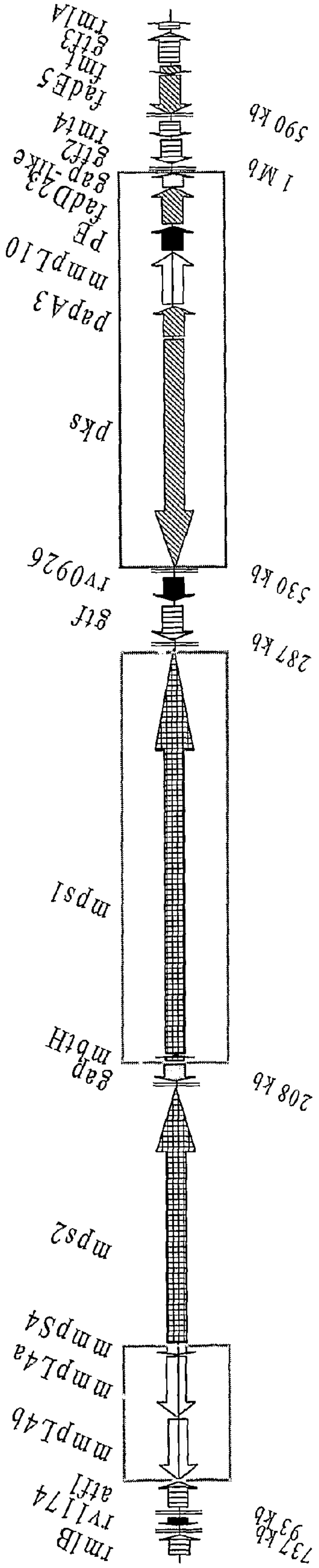

FIG. 3. Genetic organization of the L5P locus in *M. avium* subsp. *paratuberculosis* (Map). Arrows comprising a single horizontal line are members of the mmpSL family, arrows comprising vertical horizontal lines are involved in sugar biosynthesis, activation, transfer and modification, arrows comprising diagonal lines are involved in lipid biosynthesis, activation.

Figure 4:
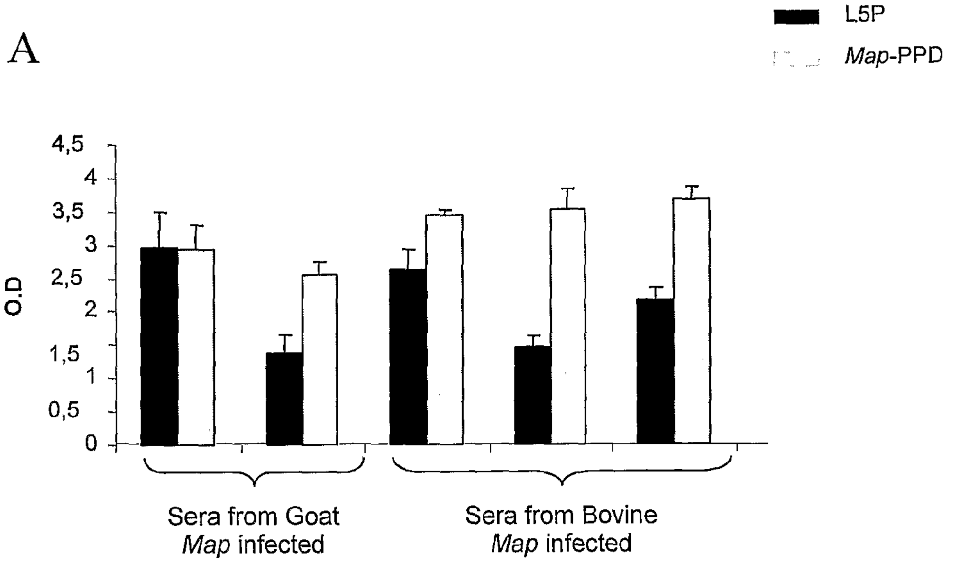
Figure 4:
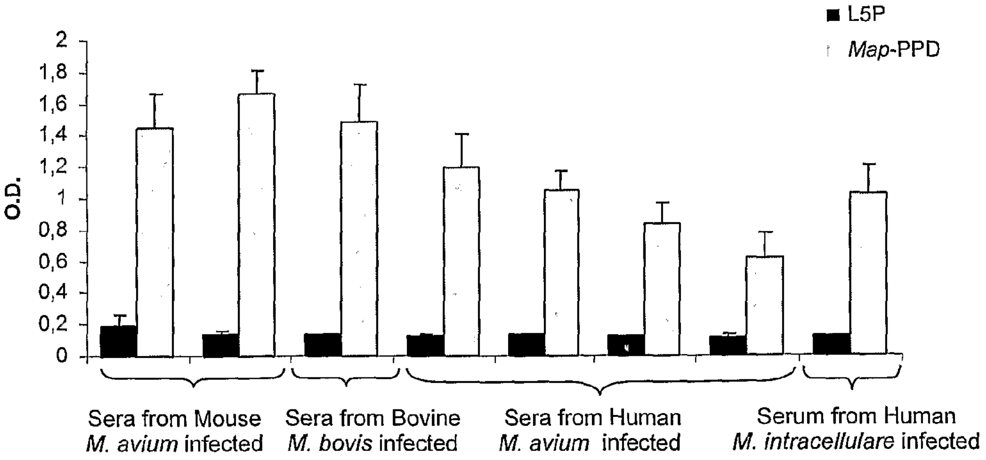

FIG. 4. Immunogenicity of the L5P. A). ELISA performed on lipopentapeptide (L5P) and purified protein derivatives (PPD) using sera from *M. avium* subsp. *paratuberculosis*-naturally infected bovines and goats B). ELISA performed on L5P and PPD using sera from *M. avium* subsp. *avium*-experimentally infected mouse, sera from *M. bovis*-naturally infected bovines, sera from *M. avium* subsp. *avium*- and *M. avium* subsp. *intracellulare*-naturally infected humans. The results are expressed as the means of triplicates.

Figure 5:
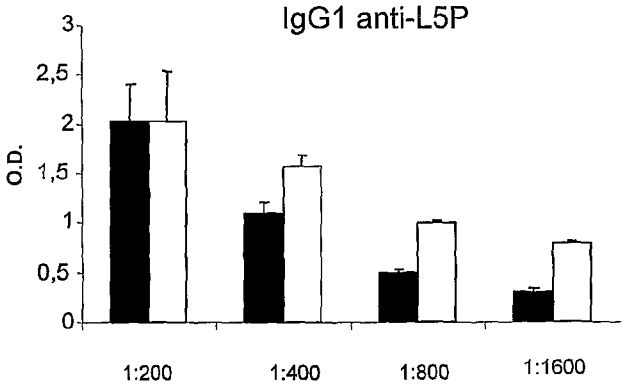
Figure 5:
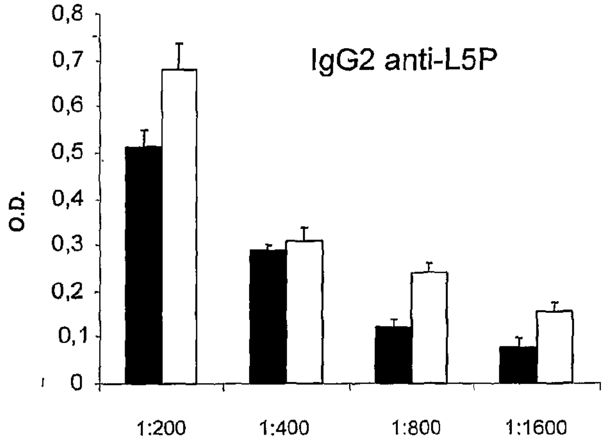
Figure 5:
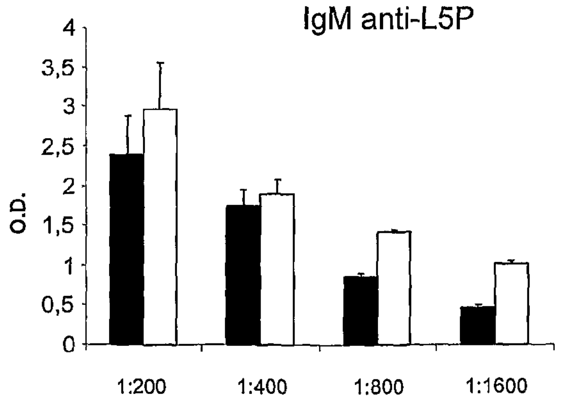

FIG. 5. Isotyping the Ig in sera of *M. avium* subsp. *paratuberculosis* (Map) infected animals. A) Anti-lipopentapeptide (L5P) IgG1 antibody activity, B) Anti-L5P IgG2 antibody activity and C) Anti-L5P IgM antibody activity. Serial 2-fold dilution of reactive sera from two different bovines naturally Map-infected. Each animals in represented by a distinct colour.

Figure 6:
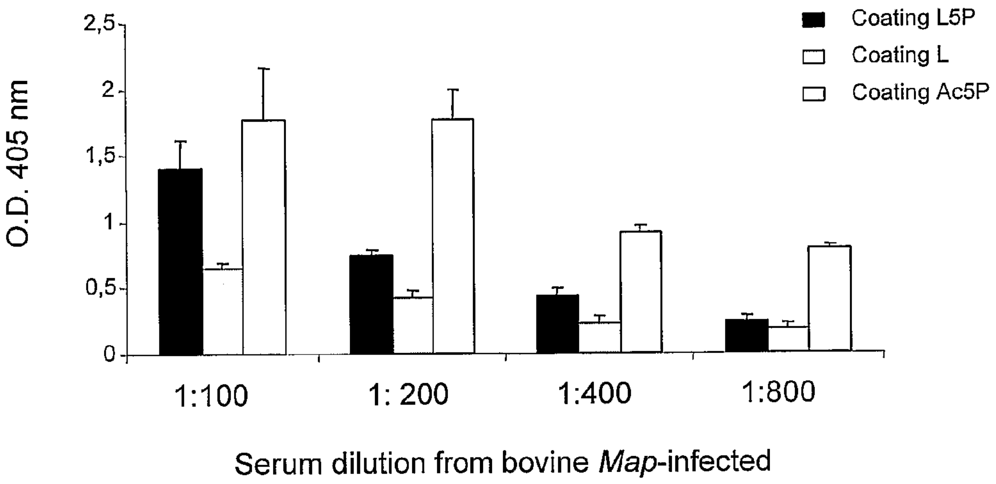
Figure 6:
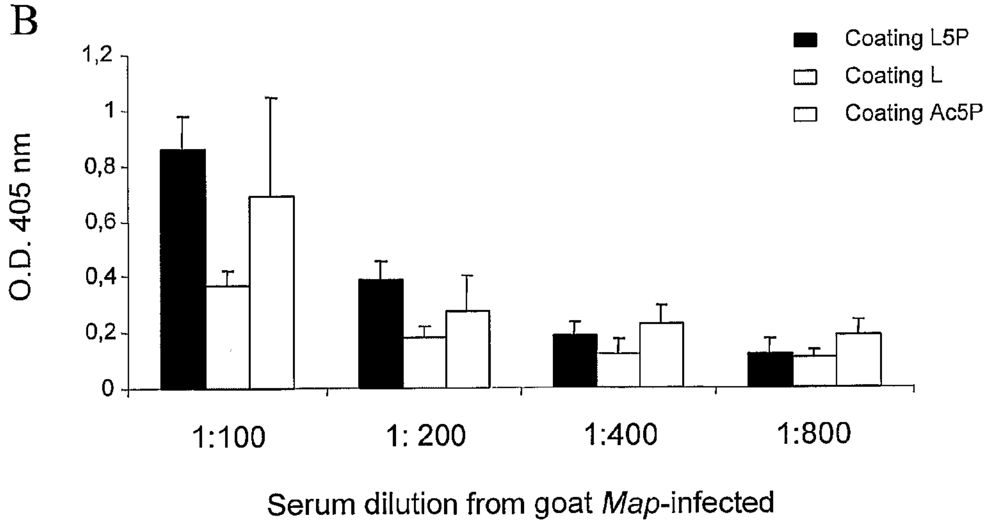

FIG. 6. Immunoreactivity of the pentapeptidyl (5P) or the lipid moieties of the lipopentapeptide. A) *M. avium* subsp. *paratuberculosis*-(Map) naturally infected bovines B) Map naturally infected goats. Serial 2-fold dilution of reactive sera from two animals naturally Map infected.

Figure 7:
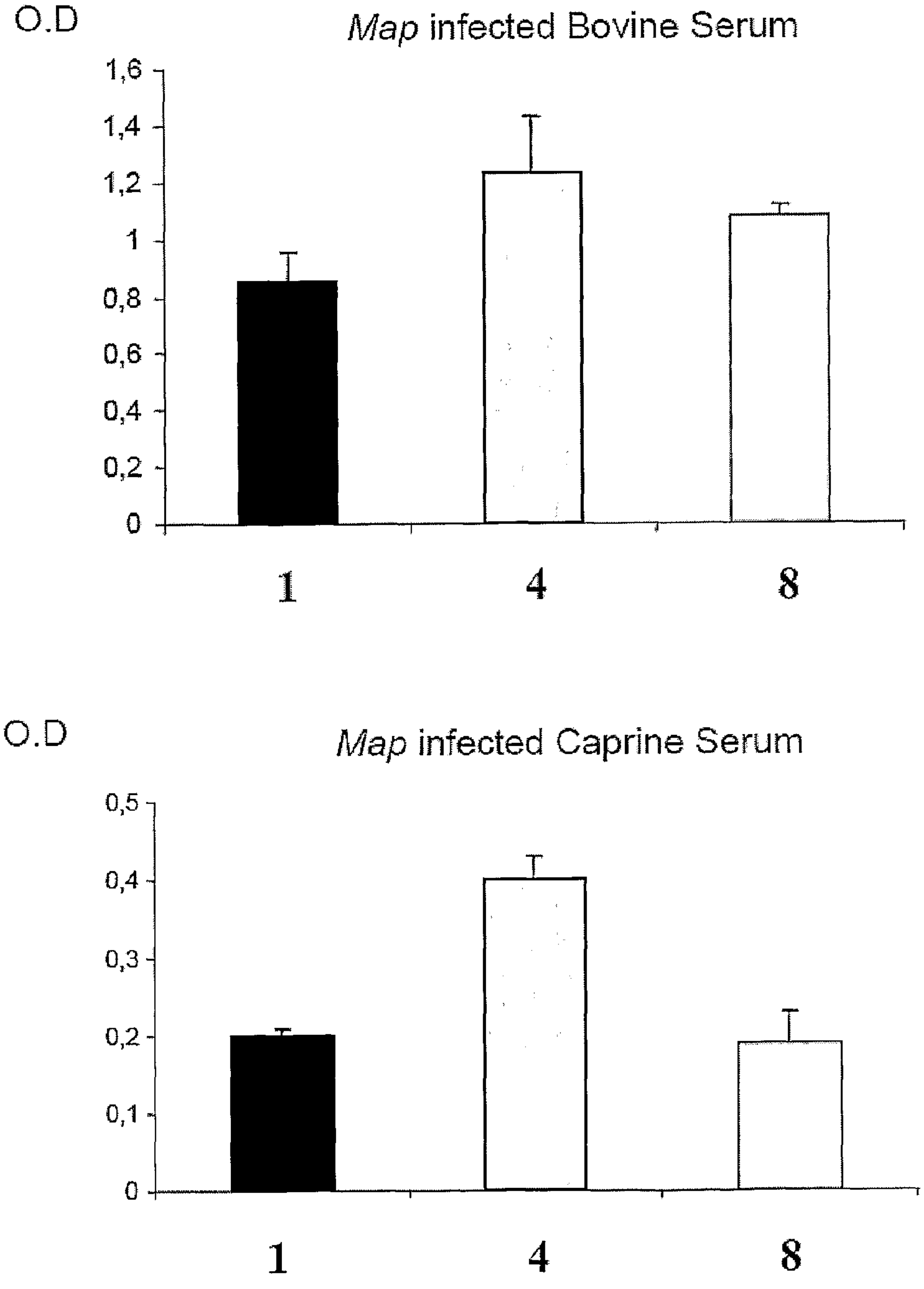

FIG. 7. Antigenicity of the L5P and derivatives. ELISA was performed on lipopentapeptide 1 (L5P), derivatives 4 (SEQ ID NO: 1) and 8 (SEQ ID NO: 10) using sera from *M. avium* subsp. *paratuberculosis* naturally infected bovines and goats. The results are expressed as the means of triplicates.

EXAMPLE 1

Production of a Lipopentapeptide is a Signature of the Map Strains

To test whether all Map strains produce lipopeptides, a large panel of Map isolates (see Table 1) was analysed. This Map collection consists in isolates originating from various animals (cattle, sheep, goat, red deer, rabbit) and humans and from various geographical origins (Argentina, Czech Republic, Italia, Netherlands, UK, USA, Slovenia) (THIBAULT et al., J Clin Microbiol, 45, 2404-2410, 2007). To add a level of strain diversity, isolates having distinct mini satellite and RFPL (E900) profiles were included. *M. smegmatis* $mc^2155$ and Mav 104 were also both included as control strains producing GPL.

*M. smegmatis* $mc^2155$, Mav strains and Map strains were all cultured in 7H9 supplemented with 10% ADC at 37° c. For Map, Mycobactin J (2 μg/ml) (Institut Pourquier, Montpellier, France) was also added. All bacterial cultures were grown to stationary phase. Mav 104 and Map K-10 were supplied by R. Barletta of the University of Nebraska.

Lipids were extracted from cells with a mixture of chloroform and methanol as previously described (VILLENEUVE et al., J Biol Chem, 278, 51291-51300, 2003). GPLs and lipopeptides were identified by thin-layer chromatography (TLC) on silica gel Durasil 25-precoated plates (Macherey-Nagel) run in chloroform-methanol (90:10 and 96:4 [vol/vol], respectively) (VILLENEUVE et al., J Biol Chem, 278, 51291-51300, 2003. The sugar-containing GPLs were revealed by spraying plates with 0.2% anthrone in concentrated sulfuric acid (ETIENNE et al., Microbiology, 148, 3089-3100, 2002) whereas the lipopeptides were detected using 10% copper sulfate in 8% phosphoric acid; then the lipids were visualized by heating at 110° C. Identification of the lipids was confirmed by matrix-assisted laser-desorption/ionization-time of flight (MALDI-TOF) mass spectrometry analysis.

As shown in FIG. 1A, Ms and Mav strains produced GPLs-like lipids. All the GPLs-associated pseudomolecular ions ($[M+Na]^+$) detected in these strains perfectly matched with the calculated molecular weight of the GPLs previously described for these strains (FIG. 2) (ETIENNE et al., Microbiology, 148, 3089-3100, 2002; ECKSTEIN et al., J Biol Chem, 281, 5209-5215, 2006; MCNEIL et al., J Biol Chem 262(6):2630-5, 1987; BRENNAN et al., J Biol Chem 254(14) 4205-11, 1979).

Accordingly, the GPLs produced by Ms corresponded mainly to the diglycosylated form of the non-specific GPLs (nsGPLs), which confirms earlier reports (VILLENEUVE et al., J Biol Chem, 278, 51291-51300, 2003; ETIENNE et al., Microbiology, 148, 3089-3100, 2002). Mav 104 (serotype 1) produced apolar nsGPLs, but also triglycosylated serovar-specific GPLs (ssGPLs) (Table 2). Interestingly, none of the Map strains tested produced GPLs as assessed by TLC (FIG. 1A). This lack of GPLs production was observed even when specialized techniques of lipid extraction that have been adapted to Map were used (CAMPHAUSEN et al., Proc Natl Acad Sci USA, 82, 3068-3072, 1985).

These lipid extracts were also analyzed using MALDI-TOF mass spectrometry, a highly sensitive and accurate method to detect and characterize parietal metabolites. No pseudomolecular ion possibly corresponding to GPLs was detected in the Map lipid extracts, confirming the TLC results. However, a pseudomolecular $[M+Na]^+$ ion peak was readily detectable at m/z 940.73 atomic mass units (FIG. 2). This signal, accounting for the lipopentapeptide Para-LP-01 described in Map K-10 (ECKSTEIN et al., J Biol Chem, 281, 5209-5215, 2006), was detected in all Map strains including the vaccine strain 316F. This prompted us to analyze the lipid extracts of all the Map strains using the TLC conditions reported by ECKSTEIN et al to be specific of Para-LP-01. A Para-LP-01-like compound was detected in all the Map strains (FIG. 1B and data not shown), even if the spot was barely detectable in some cases (e.g. line 2 or 4-6, FIG. 1B). This compound was purified according to ECKSTEIN et al (FIG. 1B) and analyzed by MALDI-TOF mass spectrometry. It displayed a major pseudomolecular $[M+Na]^+$ ion peak at m/z 940.73 plus minor ion peaks differing by 14 atomic mass units, i.e. one methylene unit (data not shown), which could be assigned to the variability in the chain length of the fatty acyl moiety of the lipopentapeptide. These molecules were alkali stable (data not shown) a feature of lipids with N-linked fatty acyl groups such as GPLs and lipopeptides (BELISLE et al., J Biol Chem, 268, 10517-10523, 1993). Finally, the $^1H$ NMR spectrum of the purified lipopentapeptide look identical to that of synthetic L5P (see below) and to that published by ECKSTEIN et al. (data not shown). This set of experiments confirms that Map does not produce GPLs but produces instead lipid compounds with a mass compatible with the lipopentapeptides that have been described in the past (LANEELLE and ASSELINEAU, Biochim Biophys Acta, 59, 731-732, 1962; OHENE-GYAN et al., Comp Immunol Microbiol Infect Dis, 18, 161-170, 1995; CAMPHAUSEN et al., Proc Natl Acad Sci USA, 82, 3068-3072, 1985; LANEELLE et al., Bull Soc Chim Biol (Paris), 2133-2134, 1965; ECKSTEIN et al., J Biol Chem, 281, 5209-5215, 2006).

In conclusion, the analysis of this large panel of clinical strains showed that the production of a lipopentapeptide is a signature of the subspecies *paratuberculosis* that easily distinguishes it from Mav.

EXAMPLE 2

Identification of the Genetic Locus Involved in the Synthesis of Lipopeptides Map Strains All the Mav strains are characterized by the production of glycopeptidolipid, while, as shown above only the Map strains produce a lipopentapeptide. One can notice the structural relatedness between the GPL and the lipopentapeptide, both being composed of a fatty acyl moiety N-linked to a short oligopeptide, of which the first amino-acid is a phenylalanine of the D series. On the other hand, a number of differences can be seen. First, the lipopentapeptide is made of 5 amino acids, none of them containing free hydroxyl group. Second, by contrast with GPL, the lipopentapeptide fatty acid is shorter, saturated and is not methylated. The GPL locus is well described in Mav and in a number of rapid growing mycobacteria. We consequently investigated whether a GPL-like locus was present in Map.

In most cases, an ortholog of each building blocks of the GPL biosynthesis was present in Map. This was the case for the pks-gap like region that plays a role in the biosynthesis of the fatty acid, activation and transfer onto the peptidyl moiety. This was also the case for mmpS4, mmpLa and mmpL4b that are believed to play a role in the biosynthesis and export of the GPLs. However, a number of genes were missing or inactivated by mutation. Rmt2, and 3 that are involved in the methylation of the rhamnosyl unit in Mav were absent. The glycosyltransferase (gtf1, gtf2 and gtf3) were all present and apparently functional. The fact that the lipopentapeptide is not glycosylated likely lay in the absence of free hydroxyl group in the amino acids. The fmt gene that is involved in the methylation of the fatty acid moiety of GPLs was containing a large deletion (438/822 nt) in Map, which probably leads to an inactive enzyme. This observation is consistent with the fact that the fatty acyl moiety of the lipopentapeptide is not methylated.

The genetic organization of the L5P locus in *M. avium* subsp. *paratuberculosis* (Map) is schematized in FIG. 3.

A major distinctive feature in Map is the putative mbtH-mps1-mps2 potential operon, which is divided in 2 regions in this species. Moreover, both mps1 and mps2 genes are strikingly larger in this species, approximately 50% larger than in the GPL producing species. In Mav, but also in Ms, *M. chelonae* and *M. abscessus*, the mps1 and mps2 genes are responsible for the synthesis of the peptidyl moiety of the GPL. These genes belong to the non-ribosomal protein synthesis family (nrp). Enzymes from this family are very large (>3000 amino acids) and are involved in the synthesis of pharmaceutical compounds such as vancomycin and cyclosporine. Nrp are composed of modules that are responsible for the selection, the modification and the formation of the peptidic bonds between amino acids of the non-ribosomically synthesized peptides. The number and order of the modules usually reflect the number and the sequence of the peptide synthesized. In Ms and Mav, the mps1 and mps2 genes collectively encode 4 modules, the first three of which contain an epimerase domain that convert an L-amino acid into the non-natural D-form. Thus, the number and structure of the modules is in agreement with the structure of the tetrapeptide produced by Ms and Mav, which is D-Phe-D-allo-Thr-D-Ala-L-Alaninol. A bio-computing analysis of the domain composition of the Mps1 protein of Map K-10 shows that it is made of 5 modules and thus potentially encodes a protein having the capability of synthesizing a pentapeptide. In silico analysis of the domain composition of these modules suggests that the first amino acid should be a D-form (occurrence of an epimerase domain) and the second amino acid should be a L-form N-methylated (occurrence of a methylation domain) while the 3 other amino acids should be of an unmodified L-form. Contrary to the mps1 gene of Ms and Mav, a TE domain, which is responsible for the release of the peptidic chain (LAUTRU and CHALLIS, Microbiology, 150, 1629-1636, 2004), is clearly identifiable in Map. The Mps2 protein of Map K-10 has a module content that allows the synthesis of a tripeptide, the first amino acid should be a D-form. In conclusion, the module and the domain composition of the Mps1 and Mps2 protein of Map is dramatically different from that of Ms and Mav. Moreover, depending on whether the Mps1 and Mps2 proteins act collectively, Map has the potential to produce a lipooctapeptide (L8P) or a lipopentapeptide plus eventually a lipotripeptide.

It was next tested whether the genetic locus found in Map K-10 was also conserved in various Map isolates. Primers enabling the distinction between GPL and lipopentapeptide producers were designed and used to investigate by PCR all the strains previously characterized for lipopentapeptide production.

Oligonucleotides hybridizing with mps1 and mps2 genes (amplifying the mps1-mps2 junction) were designed: 5'mps1S as forward 5' CGA GGA CTT CGG CGA GCC GGT (SEQ ID NO: 13) and 3'mps2 as reverse 5' TCA TGT AGG CGA TGT CGT CGG GC (SEQ ID NO: 14). As a control, oligonucleotides hybridizing with the gap and the mbtH genes (amplifying the gap-mbtH junction) were also designed: gap-mbtH as forward (5' ATT GAG CGC AGC CAG CAT CCC CAA GCC C) SEQ ID NO: 15, gap-mbtH as reverse (5' TTG ACC AGG ACG AAA AAT CGG CCG CC) SEQ ID NO: 16.

The PCR mixture was composed as follows using the Go Taq Flexi DNA polymerase (Promega). Two microliters from 10 μg $ml^{-1}$ DNA solutions was added to a final volume of 25 μL containing 0.25 μL of Go Taq Flexi DNA polymerase (5 U), 5 μL of Q-solution, 0.2 mM of each dATP, dCTP, dGTP and dATP (Promega), 5 μL of 5×PCR buffer, 1 μM primers and 1.5 mM $MgCl_2$. The reactions were carried out using an iCycler thermal cycling machine (BioRad). PCR conditions were as follows: 1 cycle of 5 min at 94° C.; 40 cycles of 30 s at 94° C., 30 s at 58° C., and 30 s at 72° C.; and 1 cycle of 7 min at 72° C.

Whereas PCR amplification with 5'mps1S and 3'mps2 gives a band of the correct size (1618 bp) in GPL producers (Ms, Mav, Mai), no band is observed in the case of the Map strains. In contrast, the amplification with oligonucleotides hybridizing with the gap and the mbtH genes gives a band of the correct size (1618 bp) in all the Map strains tested. The absence of amplification in Map is due to the long distance separating mps1 and mps2 genes in this subspecies. These data show that the mps1 and mps2 genes are disconnected in all Map strains tested and suggest that this peculiar genomic organisation is a signature of Map strains, despite the variability existing among isolates (mini satellite and RFLP).

Another objective was to ascertain that L5P is produced by the whole Map subspecies including pig and sheep isolates of the S type. Therefore we collected S type strains and performed PCR on the putative L5P locus. As described previously the amplification with oligonucleotides hybridizing with the gap and mbth genes gives a band of size 1618 bp corresponding to the L5P locus which is a signature of Map subspecies. This result suggests that L5P is produced also in atypical S type strains and may be used in diagnostic tests for all the Map subspecies.

In conclusion, this analysis shows that the Map subspecies can be easily distinguished from the Mav subspecies by a simple PCR assay and that this organization strictly correlates with the production of the lipopentapeptide.

EXAMPLE 3

The Lipopentapeptide is the Target of a Specific Humoral Immune Response in Map Infected Animals A small amount of lipopentapeptide was purified from a Map culture in order to evaluate its reactivity against sera of infected animals.

The lipopentapeptide was purified as previously described by Belisle et al (BELISLE et al., J Biol Chem, 268, 10510-10516, 1993) with some modifications. Briefly, after extraction of the lipids from the cell pellets (VILLENEUVE et al., J Biol Chem, 278, 51291-51300, 2003), the total washed lipid fraction was hydrolyzed with 0.1 N KOH at room temperature to select for alkali-stable lipids. These lipids were then chromatographed on a Florisil (60-100 mesh) column (1.5×25-cm) irrigated with chloroform and then with a stepwise gradient of increasing concentrations of methanol in chloroform. The purification of the lipopeptide was achieved from the 2% methanol fraction in chloroform by preparative thin-layer chromatography (ECKSTEIN et al., J Biol Chem, 281, 5209-5215, 2006).

The purified lipopentapeptide showed a high reactivity against the sera (data not shown) suggesting a potential usefulness in paratuberculosis diagnosis. However, there were two major drawbacks. First, the purified lipopentapeptide was only 85% pure and thus it could not be excluded that the sero-reactivity was due to contaminants. Second, purifying the lipopentapeptide was really a challenging task and the recovery yield was not compatible with a high-throughput diagnostic technology. To circumvent these problems, the lipopentapeptide was chemically synthesized by solid phase peptide synthesis using the Fmoc chemistry, which allows the large-scale production of pure lipopentapeptide.

Synthesis of L5P

The lipopeptide (L5P) was synthesized manually using the standard Fmoc chemistry protocol on a 4-hydroxymethylbenzoyl resin (HMBA-AM resin, Novabiochem). The eicosanoic acid (L) was purchased from Acros Organics. Briefly, the C-terminal amino acid (Fmoc-Ala-OH) was attached to the resin using the symmetrical anhydride (5 equiv). After 30 min coupling, the resin substitution was estimated by UV analysis of a resin sample. After capping with $Ac_2O$ in DMF, the following $N^{\alpha}$-Fmoc protected amino acids and the eicosanoic acid (3 equiv.) were incorporated to the peptide chain using DMF as solvent and 2-(1H-9-azabenzotriazole-1-yl)-1,1,3,3-tetramethyluronium hexafluorophosphate (HATU)/N,N-diisopropylethylamine (DIEA) as the coupling reagents. Fmoc protection was removed with 20% piperidine in DMF. The product was cleaved from the resin in DMF/MeOH/DIEA (5/5/1 v/v/v) during 16 hours at 60° C. After purification of the crude product on a silica gel column using $CH_2Cl_2$/MeOH as eluent (from 100/0 to 97/3), 27 mg of the lipopeptide L5P were obtained (yield 60% based on the Fmoc-Ala-resin substitution).

The compound was characterized by mass spectrometry (Q-T of Micro Waters) and NMR (Bruker 400 MHz instrument). Although the mass and the $^1H$ NMR spectra look identical to those published by ECKSTEIN et al, several discrepancies in the NMR signal assignments were found. We report below our detailed assignments.

ESMS for $C_{54}H_{87}N_5O_7$ (calcd 917.6606) m/z 918.6778 [$M+H^+$], 940.6540 [$M+Na^+$].

$^1H$ NMR (MeOD): δ 0.53 (d, 1H, $CH_3\gamma$ Val, J=6.63 Hz), 0.79-0.83 (m, 9H, $CH_3\gamma$ Val, $CH_3\delta$ Ile, $CH_3\gamma$ Ile), 0.93 (t, 3H, $CH_3$ lipid, J=6.6 Hz), 1.03 (m, 1H, $1CH_2\gamma$ Ile), 1.22-1.35 (m, 33H, 16 $CH_2$ lipid, $1CH_2\gamma$ Ile), 1.37 (d, 3H, $CH_3\beta$ Ala, J=7.27 Hz), 1.45-1.55 (m, 2H, $CH_2CH_2CO$ lipid), 1.77 (m, 1H, CHβ Ile), 2.06-2.21 (m, 3H, $CH_2CO$ lipid, CHβ Val), 2.88-2.96 (m, 2H, $1CH_2\beta$ D-Phe, $1CH_2\beta$ Phe), 3.04 (s, 3H, $NCH_3$), 3.02-3.05 (1H, $1CH_2\beta$ D-Phe), 3.12-3.17 (dd, 1H, $1CH_2\beta$ Phe, $J_{1CH2\beta,1CH2\beta}$=14.03 Hz), 3.70 (s, 3H, $OCH_3$), 4.19 (d, 1H, CHα Ile, J=7.45 Hz), 4.40 (q, 1H, CHα Ala), 4.46 (d, 1H, CHα Val, J=11.02 Hz), 4.69 (dd, 1H, CHα Phe, $J_{CH\alpha,1CH2\beta}$=5.69 Hz, $J_{CH\alpha,1CH2\beta}$=8.74 Hz), 5.19 (t, 1H, CHα D-Phe, J=7.58 Hz), 7.18-7.28 (10H, Ph).

$^{13}C$ NMR (MeOD): δ 10.31 ($CH_3\delta$ Ile), 13.41 ($CH_3$ lipid), 14.93 ($CH_3\gamma$ Ile), 16.50 ($CH_3\beta$ Ala), 18.07, 19.10 ($CH_3\gamma$ Val), 22.71 ($CH_2$ lipid), 24.62 ($CH_2\gamma$ Ile), 25.84 ($CH_2CH_2CO$ lipid), 26.41 (CHβ Val), 29.24, 29.42, 29.44, 29.53, 29.69, 29.75, 32.05 ($CH_2$ lipid), 30.67 ($NCH_3$), 35.75 ($CH_2CO$ lipid), 37.09 (CHβ Ile), 37.83 ($CH_2$β Phe), 38.43 ($CH_2$βD-Phe), 48.42 (CHα Ala), 51.09 (CHα D-Phe), 51.73 ($OCH_3$), 54.49 (CHα Phe), 57.69 (CHα Ile), 63.29 (CHα Val), 128.10, 128.36, 129.81, 129.99, 130.76, 130.85, 138.37, 138.67 (Ph), 171.98 (CO Val), 173.32 (CO Phe), 173.55 (CO Ile), 174.67 (CO Ala), 175.32 (CO D-Phe), 175.77 (CO lipid).

To test whether the synthetic L5P was recognized by the serum of infected animals, it was tested in ELISA against a panel of sera from animal infected either by Map or by *M. bovis* or by Mav. Human sera from patients infected by Mav and Mai were used as a negative control. PPD (Partially Purified Derivative), a crude cell wall extract of Map widely employed as a paratuberculosis diagnostic test, was also used as a positive control. The PPD was produced from samples obtained from Centraal Diergeneeskundig Instituut, Lelystad, The Netherlands. The PPD was prepared using the method of Seibert F B, Am Rev Tuberc, 44: 9-24, 1941.

For further isotyping the immunoglobulin produced against the L5P, a panel of secondary antibodies recognizing specifically either IgA, IgM, IgG1 or IgG2 antibodies was used.

ELISA Assay.

Sera were obtained from ruminants infected by Map or by *M. bovis*. Diagnoses were established by ELISA (Bovigam Prionics Zurich Switzerland and ELISA Paratuberculosis, Institut Pourquier Montpellier France) and positive culture for Map or *M. bovis*. Sera from human infected by Mav or by Mai were provided by Pr. Alain Goudeau (Hôpital Bretonneau, Tours, France). For ELISA, Maxisorp microtiter plates (Nunc, Roskilde, Denmark) were coated with 50 μL of PPD at 25 mg/ml in PBS at 37° C. overnight or 50 μg of synthetic L5P suspended in methanol were loaded into each well and air-dried. Twofold serial dilutions of antisera in PBS/Tween containing 0.5% (w/v) gelatine were added to the PPD or L5P-coated plates. The plates were then washed five times with PBS/Tween and incubated for 90 min at 37° C. with 50 μL of peroxidase-conjugated anti-ruminant-IgG (Dr. Bommeli AG, Bern, Schweiz) in a 1/600 dilution, peroxidase-conjugated sheep anti-bovine-IgM (Serotec Oxford, UK) (1/100,000), IgG Horseradish peroxidase-conjugated goat anti-human-Ig, (GAHu/Ig/PO Nordic Immunological Laboratories, The Netherlands) (1/500), mouse anti-bovine-IgG1 (KPL Gaithersburg, Md., USA) (1/5,000), mouse IgG2 (KPL Gaithersburg, Md., USA) (1/200) and mouse anti-bovine/ovine-IgA (Serotec Oxford, UK) (1/250) and incubated 90 min at 37° C. with 50 μL of peroxidase-conjugated goat anti-mouse IgG+IgM (H+L) (Jackson Immunoresearch, Baltimore, USA). Plates were washed five times with PBS/Tween, and 50 μL of peroxidase substrate were added. The reaction was stopped with 50 μL of 2 N HCl, and the plates were read photometrically at 414 nm.

As shown in FIG. 4A, sera from Map infected animals reacted with the synthetic L5P (OD above 1,5) and the sensitivity was similar to PPD. By contrast, no significant O.D. (O.D. below 0.2) was obtained with sera from *M. bovis* infected bovine or from Mav- or Mai-infected human patients, in contrast to PPD that was reacting with all these sera, demonstrating the very low specificity of this test. We furthermore tested mouse that were Mav experimentally infected and in all cases, theirs sera were cross-reacting with PPD, while none was reacting with L5P (FIG. 4B).

In conclusion, the L5P shows a sensitivity, which is similar to PPD antigen, but proves to be by far more specific than the PPD, enabling the specific and low-cost diagnosis of Map infection.

Whereas no IgA was detected (data not shown), a composite mixture made of IgM, IgG1 and IgG2 was present in the sera of the infected animals (FIG. 5).

EXAMPLE 4

The Humoral Response Involves IgM, IgG1 and IgG2 and Targets the Pentapeptidyl Moiety of the L5P We next aimed at determining the moiety of the L5P that was the predominant target of the host humoral response. An acetylated peptide (Ac5P) was obtained with a similar protocol to that used for L5P, with a final acetylation instead of the last coupling step with the eicosanoic acid.

L5P, Ac5P, and the eicosanoic acid moiety of L5P were individually tested against sera of Map-infected animals. The results are shown on FIG. 6.

ELISA of sera from bovine or goat that are Map-infected showed that the peptide moiety is highly reactive. The acetylated pentapeptide was recognized as efficiently as the L5P by the Map-infected animals. In some cases, the pentapeptide was even better recognized than the whole L5P. Consistent with this observation the lipid moiety was poorly recognized by the host sera (FIG. 6). In conclusion, this set of experiments demonstrates that the major epitopes of the L5P are peptide-based.

EXAMPLE 5

Preparation and Testing of L5P Analogues

In order to optimize the Map-specific diagnostic test, ie to improve the sensitivity and the specificity of the detection, interest was focused on the identification of the best synthetic mimic of the native Map antigen(s) (ie the "necessary and sufficient" chemical structure), starting from the L5P as the "reference compound", Therefore, several analogues (see Table 3) of the lipopentapeptide L5P were prepared by performing specific modifications of its chemical structure.

The recognition of compounds 4 (5P: free N-terminal amino group; SEQ ID NO: 1), 8 (SEQ ID NO: 10) and 9-10 (SEQ ID NO: 20 and 12) (free C-terminal carboxylic group) was analyzed by ELISA. These analyses using Map specific anti serum from infected bovine and caprine indicated that all compounds react specifically. The best antigenic response was obtained with compound 4 (5P) that may be retained as an hapten for protein conjugation in order to improve the sensitivity of the immunoassay. Preliminary results suggest that, as compared to L5P (1), 5P (4) allows a higher sensitivity for the detection of Map-specific antibodies (FIG. 7).

TABLE 1

Description of the *M. avium* subsp. *paratuberculosis* (Map) strains used in this study

| N° | Map Strains lab number | Host origin | Country origin | Minisatellite[1] profiles | IS900 RFLP[1] Profiles |
|---|---|---|---|---|---|
| 1 | (K-10) ATCC BAA-968 | Bovine | USA | INVM 2 | R01 |
| 2 | ATCC 19698 | Bovine | USA | INVM 2 | R01 |
| 3 | (Linda) ATCC 43015 | Human | USA | INVM 2 | R10 |
| 4 | 7912 | Bovine | France | INVM9 | R01 |
| 5 | 316F[2] Weybridge | Bovine | UK | INVM 17 | R01 |

TABLE 1-continued

Description of the *M. avium* subsp. *paratuberculosis* (Map) strains used in this study

| N° | Map Strains lab number | Host origin | Country origin | Minisatellite[1] profiles | IS900 RFLP[1] Profiles |
|---|---|---|---|---|---|
| 6 | 316F[2] Mérial | Bovine | France | INVM 2 | C7 |
| 7 | 13 | Bovine | France | INVM 6 | R01 |
| 8 | 20 | Bovine | France | INVM 2 | C18 |
| 9 | 47 | Bovine | France | INVM 7 | C18 |
| 10 | 54 | Bovine | France | INVM 4 | R01 |
| 11 | 60 | Bovine | France | INVM 5 | C2 |
| 12 | 64 | Bovine | France | INVM 6 | R01 |
| 13 | 85 | Bovine | France | INVM 3 | R01 |
| 14 | 104 | Bovine | France | INVM 2 | R01 |
| 15 | 115 | Bovine | France | INVM 2 | C |
| 16 | 159 | Bovine | France | INVM 8 | R01 |
| 17 | 186A | Caprine | France | INVM 1 | R01 |
| 18 | 190 | Caprine | France | INVM 1 | R01 |
| 19 | 199 | Ovine | France | INVM 2 | R01 |
| 20 | 200 | Ovine | France | INVM 2 | R24 |
| 21 | 201 | Human | Netherland | INVM 9 | R01 |
| 22 | 205 | Bovine | Sweden | INVM 13 | R13 |
| 23 | 210 | Bovine | Netherland | INVM 2 | R35 |
| 24 | 218 | Bovine | Netherland | INVM 2 | R25 |
| 25 | 220 | Bovine | Netherland | INVM 2 | R01 |
| 26 | 225 | Bovine | Argentina | INVM 1 | R09 |
| 27 | 226 | Bovine | Argentina | INVM 11 | R31 |
| 28 | 231 | Red deer | Czech Republic | INVM 1 | R34 |
| 29 | 234 | Bovine | Venezuela | INVM 3 | R04 |
| 30 | 247 | Fallow Deer | Czech Republic | INVM 34 | R10 |
| 31 | 267 | Rabbit | UK | INVM 33 | R01 |
| 32 | 282 | Bovine | Italia | INVM 2 | R01 |
| 33 | 284 | Bovine | Venezuela | INVM 3 | R04 |
| 34 | 286 | Bovine | Slovenia | INVM 33 | R06 |
| 35 | 289 | Rabbit | UK | INVM 33 | R09 |
| 36 | 290 | Bovine | Netherland | INVM 33 | R09 |
| 37 | 304 | Deer | Argentina | INVM 8 | R10 |
| 38 | 310 | Bovine | Netherland | INVM 2 | R22 |
| 39 | 335 | Bovine | Netherland | INVM 1 | R24 |
| 40 | 6756 | Ovine | New Zealand | ND | S1 |
| 41 | 6758 | Ovine | New Zealand | ND | S1 |
| 42 | P133/79 | Ovine | Faeroe Island | ND | S3 |
| 43 | 6759 | Ovine | New Zealand | ND | S5 |
| 44 | 85/14 | Ovine | Canada | ND | S6 |
| 45 | LN20 | Porcine | Canada | ND | S2 |

[1]Typing method has been described in Thibault et al.(THIBAULT et al., J Clin Microbiol, 45, 2404-2410, 2007)

[2]Vaccine strain

TABLE 2

Identification of the lipid metabolites produced by the mycobacterial strains by MALDI-TOF mass spectrometry.

| | Major pseudomolecular ion ([M + Na]+) peaks | | | |
|---|---|---|---|---|
| | nsGPLs | ssGPLs | lipopentapeptide diglycosylated form | triglycosylated form |
| Ms | 1257.90 | ns | nd | nd |
| Mav | 1295.93 | nd | 1574.09 | nd |
| Map | nd | nd | nd | 940.73 |

ns, not significant, nd, not detected.

Ms, *M. smegmatis*,

Mav, *M. avium* subsp. *avium* 104,

Map, *M. avium* subsp. *paratuberculosis* K10.

TABLE 3

Chemical Variants of L5P.

| Synthetic antigen (Abreviation)[a] | Derivative number | SEQ ID NO: | Objective to test: |
|---|---|---|---|
| LipidC20-DPhe-NMeVal-Ile-Phe-Ala-OMe (L5P) | 1[b] | 17 | Reference compound |

TABLE 3-continued

Chemical Variants of L5P.

| Synthetic antigen (Abreviation)[a] | Derivative number | SEQ ID NO: | Objective to test: |
|---|---|---|---|
| **AcNH**-DPhe-NMeVal-Ile-Phe-Ala-OMe (Ac5P) | 2[b] | 9 | Specificity attributable to the lipid? |
| LipidC20 (L)[c] | 3[b] | N/A | Specificity attributable to the peptide backbone? |
| **DPhe**-NMeVal-Ile-Phe-Ala-OMe[e] (5P) | 4 | 1 | Specificity attributable to the lipid? |
| LipidC20-**Phe**-NMeVal-Ile-Phe-Ala-OMe | 5 | 18 | Specificity attributable to the (D)Phe? |
| **AcNH**-**Phe**-NMeVal-Ile-Phe-Ala-OMe | 6 | 11 | Specificity attributable to the lipid and (D)Phe? |
| LipidC20-DPhe-**Val**-Ile-Phe-Ala-OMe | 7 | 19 | Specificity attributable to the (NMe)Val? |
| **AcNH**-DPhe-**Val**-Ile-Phe-Ala-OMe | 8 | 10 | Specificity attributable to the |

TABLE 3-continued

Chemical Variants of L5P.

| Synthetic antigen (Abreviation)[a] | Derivative number | SEQ ID NO: | Objective to test: |
|---|---|---|---|
| | | | lipid and (NMe)Va? |
| LipidC20-DPhe-NMeVal-Ile-Phe-**Ala** | 9 | 20 | Specificity attributable to the methyl ester? |
| **AcNH**-DPhe-NMeVal-Ile-Phe-**Ala** | 10 | 12 | Specificity attributable to the lipid and methyl ester? |

[a]The modifications of the L5P are highlighted in bold in the subsequent analogues. The amino-acid residues belong to the L-series, unless otherwise specified;
[b]These compounds had already been described in example 4;
[c]eicosanoic acid;
[e]$NH_2$ group of the N-terminal DPhe is unsubstituted.

The invention claimed is:

1. A method of in vitro detection of specific anti-*Mycobacterium paratuberculosis* antibody comprising in a first step contacting a biological sample with an antigen for an amount of time sufficient to form an antigen-antibody complex, wherein the antigen is selected from the group consisting of:

(a) a synthetic peptide 5P having the following formula: DPhe-NMeVal-Ile-Phe-Ala-OMe (SEQ ID NO: 1);

(b) a lipopeptide L5P consisting of the synthetic peptide a) wherein the N-terminal phenylalanine residue is N-acylated with an eicosanoic acid acyl chain; and (c) a variant of peptide (a) or lipopeptide (b) which reacts with anti-*Mycobacterium paratuberculosis* antibodies, and in a second step detecting the formation of the antigen-antibody complex in said biological sample, wherein the presence of the antigen-antibody complex indicates the presence of the anti-*Mycobacterium paratuberculosis* antibody.

2. The method of claim 1, wherein said variant is selected from the group consisting of:

Phe-NMeVal-Ile-Phe-Ala-OMe (SEQ ID NO: 2);
DPhe-Val-Ile-Phe-Ala-OMe (SEQ ID NO: 3);
Phe-Val-Ile-Phe-Ala-OMe (SEQ ID NO: 4);
DPhe-NMeVal-Ile-Phe-Ala (SEQ ID NO: 5);
DPhe-Val-Ile-Phe-Ala (SEQ ID NO: 6);
Phe-Val-Ile-Phe-Ala (SEQ ID NO: 7);
Phe-NMeVal-Ile-Phe-Ala (SEQ ID NO: 8)

and their derivatives resulting from N-acylation of the N-terminal phenylalanine residue with a C1 to C30 acyl group.

3. A method of evaluating in vitro the T-cell immune response directed against *Mycobacterium paratuberculosis* in a subject comprising the steps of contacting a biological sample containing T cells isolated from the subject, with an antigen as defined in claim 1, and detecting cytokine expression by activated T-cells in the biological sample, wherein cytokine expression indicates the presence of a T cell immune response in the subject.

4. The method of claim 1, where in the antigen-antibody complex is detected using a technique selected from the group consisting of ELISA, radioimmunoassay, electrophoresis, immunofluorescence and western blot.

5. The method of claim 2, wherein said variant is selected from the group consisting of:

Phe-NMeVal-Ile-Phe-Ala-OMe (SEQ ID NO: 2);
DPhe-Val-Ile-Phe-Ala-OMe (SEQ ID NO: 3);
Phe-Val-Ile-Phe-Ala-OMe (SEQ ID NO: 4);
DPhe-NMeVal-Ile-Phe-Ala (SEQ ID NO: 5);
DPhe-Val-Ile-Phe-Ala (SEQ ID NO: 6);
Phe-Val-Ile-Phe-Ala (SEQ ID NO: 7); and
Phe-NMeVal-Ile-Phe-Ala (SEQ ID NO: 8).

6. The method of claim 2, wherein said variant is selected from the group consisting of:

Phe-NMeVal-Ile-Phe-Ala-OMe (SEQ ID NO: 2);
DPhe-Val-Ile-Phe-Ala-OMe (SEQ ID NO: 3);
Phe-Val-Ile-Phe-Ala-OMe (SEQ ID NO: 4);
DPhe-NMeVal-Ile-Phe-Ala (SEQ ID NO: 5);
DPhe-Val-Ile-Phe-Ala (SEQ ID NO: 6);
Phe-Val-Ile-Phe-Ala (SEQ ID NO: 7); and
Phe-NMeVal-Ile-Phe-Ala (SEQ ID NO: 8), wherein the N-terminal phenylalanine residue is N-acylated with a C1 to C30 acyl group.

7. The method of claim of claim 3, wherein the cyokine expression is detected using ELISPOT.

8. A composition comprising an antigen selected from the group consisting of:

(a) a synthetic peptide 5P having the following formula: DPhe-NMeVal-Ile-Phe-Ala-OMe (SEQ ID NO: 1);

(b) a lipopeptide L5P consisting of the synthetic peptide a) wherein the N-terminal phenylalanine residue is N-acylated with an eicosanoic acid acyl chain; and (c) a variant of peptide (a) or lipopeptide (b) which reacts with anti-*Mycobacterium paratuberculosis* antibodies;

wherein the antigen is present in an amount sufficient to form an antigen-antibody complex with an anti-*Mycobacterium paratuberculosis* antibody.

9. The composition of claim 8, wherein said variant is selected among the group consisting of:

Phe-NMeVal-Ile-Phe-Ala-OMe (SEQ ID NO: 2);
DPhe-Val-Ile-Phe-Ala-OMe (SEQ ID NO: 3);
Phe-Val-Ile-Phe-Ala-OMe (SEQ ID NO: 4);
DPhe-NMeVal-Ile-Phe-Ala (SEQ ID NO: 5);
DPhe-Val-Ile-Phe-Ala (SEQ ID NO: 6);
Phe-Val-Ile-Phe-Ala (SEQ ID NO: 7);
Phe-NMeVal-Ile-Phe-Ala (SEQ ID NO: 8)

and their derivatives resulting from N-acylation of the N-terminal phenylalanine residue with a C1 to C30 acyl group.

10. The composition of claim 9, wherein said variant is selected among the group consisting of:

Phe-NMeVal-Ile-Phe-Ala-OMe (SEQ ID NO: 2);
DPhe-Val-Ile-Phe-Ala-OMe (SEQ ID NO: 3);
Phe-Val-Ile-Phe-Ala-OMe (SEQ ID NO: 4);
DPhe-NMeVal-Ile-Phe-Ala (SEQ ID NO: 5);
DPhe-Val-Ile-Phe-Ala (SEQ ID NO: 6);
Phe-Val-Ile-Phe-Ala (SEQ ID NO: 7); and
Phe-NMeVal-Ile-Phe-Ala (SEQ ID NO: 8).

11. The composition of claim 9, wherein said variant is selected among the group consisting of:

Phe-NMeVal-Ile-Phe-Ala-OMe (SEQ ID NO: 2);
DPhe-Val-Ile-Phe-Ala-OMe (SEQ ID NO: 3);
Phe-Val-Ile-Phe-Ala-OMe (SEQ ID NO: 4);
DPhe-NMeVal-Ile-Phe-Ala (SEQ ID NO: 5);
DPhe-Val-Ile-Phe-Ala (SEQ ID NO: 6);
Phe-Val-Ile-Phe-Ala (SEQ ID NO: 7); and
Phe-NMeVal-Ile-Phe-Ala (SEQ ID NO: 8), wherein the N-terminal phenylalanine residue is N-acylated with a C1 to C30 acyl group.

12. The composition of claim 8 wherein the composition is an immunogenic composition.

* * * * *